(12) United States Patent
Baleine et al.

(10) Patent No.: US 8,570,505 B2
(45) Date of Patent: Oct. 29, 2013

(54) ONE-DIMENSIONAL COHERENT FIBER ARRAY FOR INSPECTING COMPONENTS IN A GAS TURBINE ENGINE

(75) Inventors: Erwan Baleine, Orlando, FL (US); Clifford Hatcher, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 0 days.

(21) Appl. No.: 13/412,920

(22) Filed: Mar. 6, 2012

(65) Prior Publication Data
US 2013/0235391 A1 Sep. 12, 2013

(51) Int. Cl.
*G01B 11/14* (2006.01)
*G01N 21/88* (2006.01)

(52) U.S. Cl.
USPC ........................................ 356/237.1; 356/625

(58) Field of Classification Search
USPC .......... 356/625, 237.1; 348/82; 385/120, 115, 385/116, 12; 250/227.11, 227.2, 239, 250/578.1, 234, 235; 415/173.7, 170.1
See application file for complete search history.

(56) References Cited

U.S. PATENT DOCUMENTS

| | | | |
|---|---|---|---|
| 3,788,143 A | | 1/1974 | Gabriel |
| 5,511,948 A | * | 4/1996 | Suzuki et al. ................. 416/191 |
| 6,315,301 B1 | | 11/2001 | Umemura et al. |
| 6,364,524 B1 | * | 4/2002 | Markham ..................... 374/131 |
| 7,231,817 B2 | * | 6/2007 | Smed et al. ................. 73/112.01 |
| 2005/0270519 A1 | * | 12/2005 | Twerdochlib .................... 356/24 |
| 2008/0101683 A1 | | 5/2008 | Zombo et al. |
| 2008/0109195 A1 | * | 5/2008 | Dischinger et al. ............... 703/7 |
| 2008/0245980 A1 | | 10/2008 | Diatzikis .................. 250/559.08 |
| 2008/0310804 A1 | * | 12/2008 | Brummel et al. ............. 385/115 |
| 2009/0148279 A1 | | 6/2009 | Shaefer et al. |
| 2009/0191050 A1 | | 7/2009 | Nereim et al. |
| 2010/0074727 A1 | | 3/2010 | Twerdochlib |
| 2010/0095678 A1 | * | 4/2010 | Hawie et al. .................... 60/752 |
| 2011/0069165 A1 | | 3/2011 | Zombo et al. |

OTHER PUBLICATIONS

RoMack inc.; Fiberoptic Bundles and Arrays; 2003; Williamsburg, VA 23188.

* cited by examiner

*Primary Examiner* — Sang Nguyen

(57) ABSTRACT

Inspecting a turbine includes positioning respective ends of a plurality of optical fibers within a high temperature region of the turbine wherein the respective first ends are aligned as a one-dimensional array. Energy emitted from an image area on a component of the turbine, is received at the ends of the optical fiber. The optical fibers convey the received energy to the other ends of the fibers that are located outside of the turbine. Outside the turbine an image of the respective other ends is captured, wherein the other ends are also aligned in a one-dimensional area. Additionally, for imaging a rotating component, a plurality of one-dimensional images of the other ends can be respectively captured at corresponding rotational positions of the component and used to create a two-dimensional image of the rotating component.

20 Claims, 4 Drawing Sheets

ONE-DIMENSIONAL COHERENT FIBER ARRAY FOR INSPECTING COMPONENTS IN A GAS TURBINE ENGINE

FIELD OF THE INVENTION

The present invention relates to the field of turbines and, more particularly to monitoring components of turbines during operation.

BACKGROUND OF THE INVENTION

In various multistage turbomachines used for energy conversion, such as turbines, a fluid is used to produce rotational motion. In a gas turbine engine, for example, air is compressed through successive stages in a compressor and mixed with fuel in a combustor. The combination of air and fuel is then ignited for generating combustion or hot working gases that are directed to turbine stages to produce the rotational motion. The compressor stages and turbine stages typically have stationary or non-rotary components, e.g., vane structures, that cooperate with rotatable components, e.g., rotor blades, for compressing air and expanding the hot working gases.

The rotor blades are typically mounted to disks that are supported for rotation on a rotor shaft. In a known construction for a turbine engine, annular disk arms extend from opposed portions of adjoining disks to define paired annular disk arms. A disk cooling air cavity is formed on an inner side of the paired annular arms between the disks of mutually adjacent stages, and a labyrinth seal may be provided on an inner surface of the stationary vane structures for cooperating with the annular arms to define a gas seal between a path for the hot working gases and the cooling air cavity. The paired annular arms extending from opposed portions of adjoining disks define opposing end faces located in spaced relation to each other forming a gap between the adjoining disks.

Typically, each of the opposing end faces forming this gap may be provided with a slot for receiving a sealing strip, also known as a "belly band" seal, which bridges the gap between the end faces to separate the cooling air flowing through the cooling air cavity from the hot working gases passing through the turbine stages. The sealing strip may be formed of multiple segments, in the circumferential direction, that are interconnected at overlapped or ship-lapped ends, as is described in U.S. Pat. No. 6,315,301, which is incorporated herein by reference.

Inaccessible or confined areas such as, for example, the gap between adjoining disks and the belly band described above, often require routine inspection to verify the integrity of internal engine parts and maintain safe operation of the engine by identifying potential problems, i.e., defects in a part, prior to failure of the part, or to identify the source of an existing problem. For example, problems may be identified through visual inspection by use of a borescope, such as during routine downtime maintenance of the gas turbine engine.

Additional monitoring of the turbine engine may be performed during operation of the engine to further identify the condition of components located within the hot gas path of the engine. While a variety of structures and materials may be incorporated into a borescope used for inspection of the interior turbine components during downtime of the turbine engine when the components are relatively cool, visual monitoring of the turbine components during operation of the turbine provides additional restrictions on the monitoring equipment. Two restrictions that exist for viewing turbine components are 1) line-of-sight configurations where various optical elements are aligned in a straight optical axis puts constraints on the location of any access port and limits the number of turbine components that are even possible to view; and 2) flexible fiber bundles that have been employed to overcome the first restriction are not suitable for the high temperature environment within some portions of a gas turbine nor are they small enough to reach all engine locations.

Accordingly, monitoring of components in turbine engines by continuous monitoring systems has generally been restricted to those locations that present substantially unobstructed access between the outer casing wall and the interior portion of the engine. Thus, there remains the need for devices and techniques to acquire images of high temperature regions of gas turbine engines so that otherwise inaccessible components can be monitored and inspected during operation of the turbine.

SUMMARY OF THE INVENTION

Accordingly, aspects of the present invention relate to methods for inspecting a turbine include positioning respective first ends of a plurality of optical fibers within a high temperature region of the turbine wherein the respective first ends are aligned as a one-dimensional array. Energy emitted from an image area on a component of the turbine, is received at the first ends of the optical fibers wherein the image area is substantially a line. The optical fibers convey the received energy to the other ends of the fibers that are located outside of the high temperature region of the turbine. Outside the turbine an image of the respective other ends is captured, wherein the other ends are also aligned in a one-dimensional array.

Additionally, for imaging a rotating component, a plurality of one-dimensional images of the other ends can be respectively captured at a corresponding rotational position of the component. From this series of one-dimensional images, a two-dimensional image of the rotating component can be created by arranging the plurality of images in order according to their respective corresponding rotational position.

Other aspects of the present invention relate to a system for inspecting a turbine that includes a plurality of optical fibers having respective first ends positioned within a high temperature region of the turbine and having respective second ends positioned outside of the high temperature region of the turbine. In particular, the respective first ends are aligned in a first one-dimensional array and the respective second ends are also aligned in a second one-dimensional array. The first one-dimensional array is configured to receive, at the respective first ends, energy emitted from an image area on a component of the turbine, the image area comprising substantially a line, wherein the plurality of optical fibers are configured to convey the energy received at the respective first ends to the respective second ends. A camera is included to capture an image of the respective second ends.

Additionally, for monitoring a rotating component that rotates based on a rotating shaft of the turbine, the system may include a shaft position signal generator which generates a position signal indicating a predetermined rotational position of the rotating shaft. There is also a trigger signal generator which transmits a trigger signal to the camera to capture the image of the second ends, wherein the trigger signal generator transmits a plurality of trigger signals to cause the camera to capture a plurality of images of the respective second ends. In particular, the trigger signal generator transmits each of the plurality of trigger signals at a respective time based on the position signal so that each respective trigger signal corresponds to a respective rotational position of the shaft. As a result an image analyzer can create a two-dimensional image of the rotating component by arranging the plurality of images in order according to the respective corresponding rotational position for each of the plurality of images.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
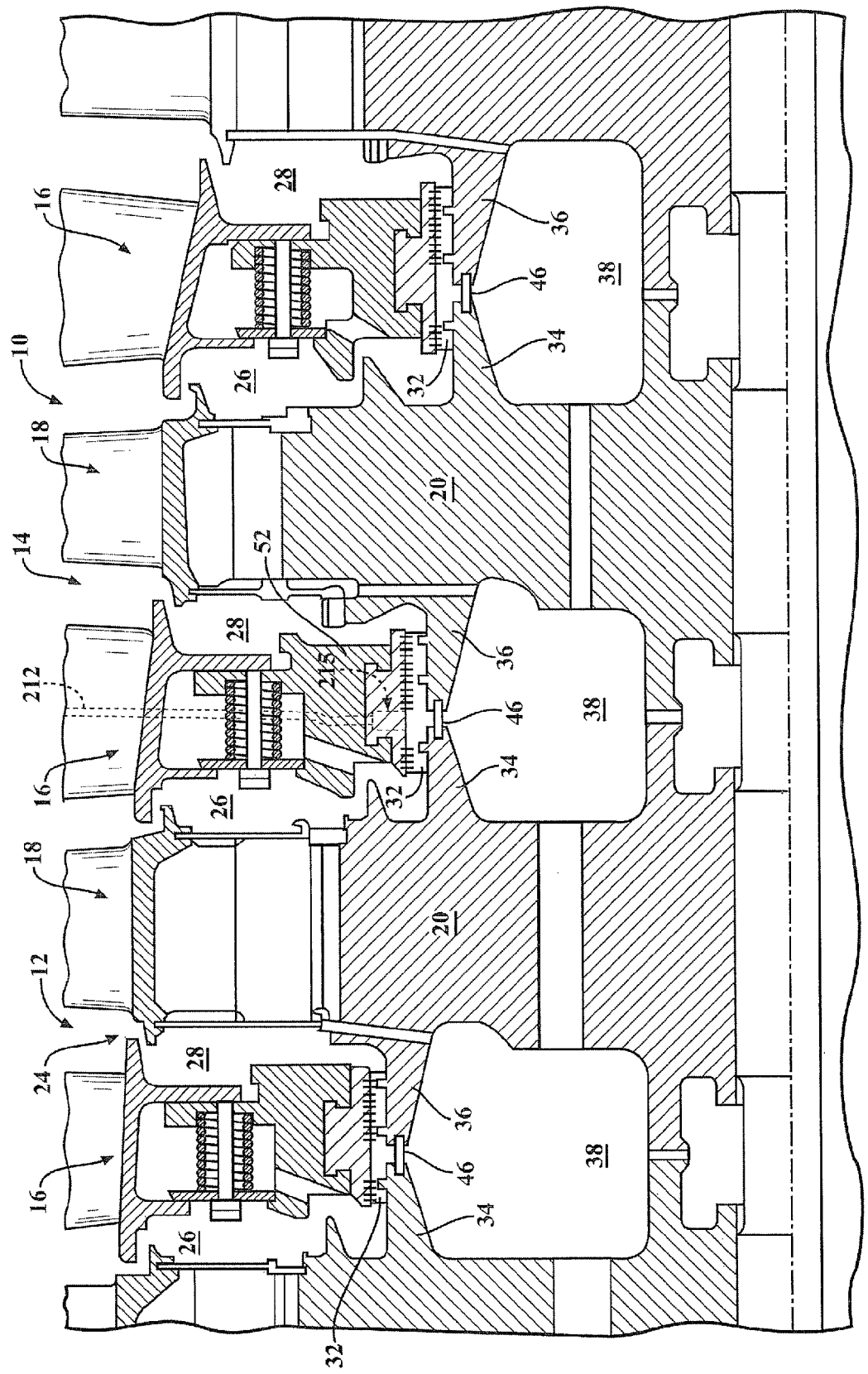
FIG. 1 is a sectional view of a turbine including a sealing band which provides an environment for imaging in accordance with the principles of the present invention.

Referring initially to FIG. 1, a portion of a turbine engine 10 is illustrated diagrammatically including adjoining stages 12, 14, each stage 12, 14 comprising an array of stationary vane assemblies 16 and an array of rotating blades 18, where the vane assemblies 16 and blades 18 are positioned circumferentially in rows within the engine 10 with alternating arrays of vane assemblies 16 and blades 18 located in the axial direction of the turbine engine 10. The blades 18 are supported on rotor disks 20 which may be secured to adjacent disks, e.g., with spindle bolts. The vane assemblies 16 and blades 18 extend into an annular gas passage 24, and hot gases, e.g., from a combustion stage, are directed through the gas passage 24 past the vane assemblies 16 and blades 18.

Disk cavities 26, 28 are located radially inwardly from the gas passage 24. Purge air is preferably provided from cooling gas passing through internal passages in the vane assemblies 16 to the disk cavities 26, 28 to cool blades 18 and to provide a pressure to balance against the pressure of the hot gases in the gas passage 24. In addition, interstage seals comprising labyrinth seals 32 are supported at the radially inner side of the vane assemblies 16 and are engaged with surfaces defined on paired annular disk arms 34, 36 extending axially from opposed portions of adjoining disks 20.

An annular cooling air cavity 38 is formed between the opposed portions of adjoining disks 20 on an inner side of the paired annular disk arms 34, 36. The annular cooling air cavity 38 receives cooling air passing through disk passages to cool the disks 20. A sealing band 46 or "belly band" seal is positioned between the annular cooling air cavity 38 and the disk cavities 26, 28.

As mentioned above, visually inspecting areas inside the turbine during operation, such as for example, around the belly band seal 46 has proven difficult because of the inaccessibility of these inner regions as well as the high temperatures (e.g., above 500° C.) in these areas. Thus, a portion 52 of the structure of the vane 16 is selected for locating a one-dimension optical fiber array that can fit within a channel in this portion 52 and can withstand the operating temperatures present near the portion 52. In particular, for example, the portion 52 generally depicted in FIG. 1, and depicted in more detail in FIG. 3, can be the interstage seal disk housing of the turbine.

Figure 2:
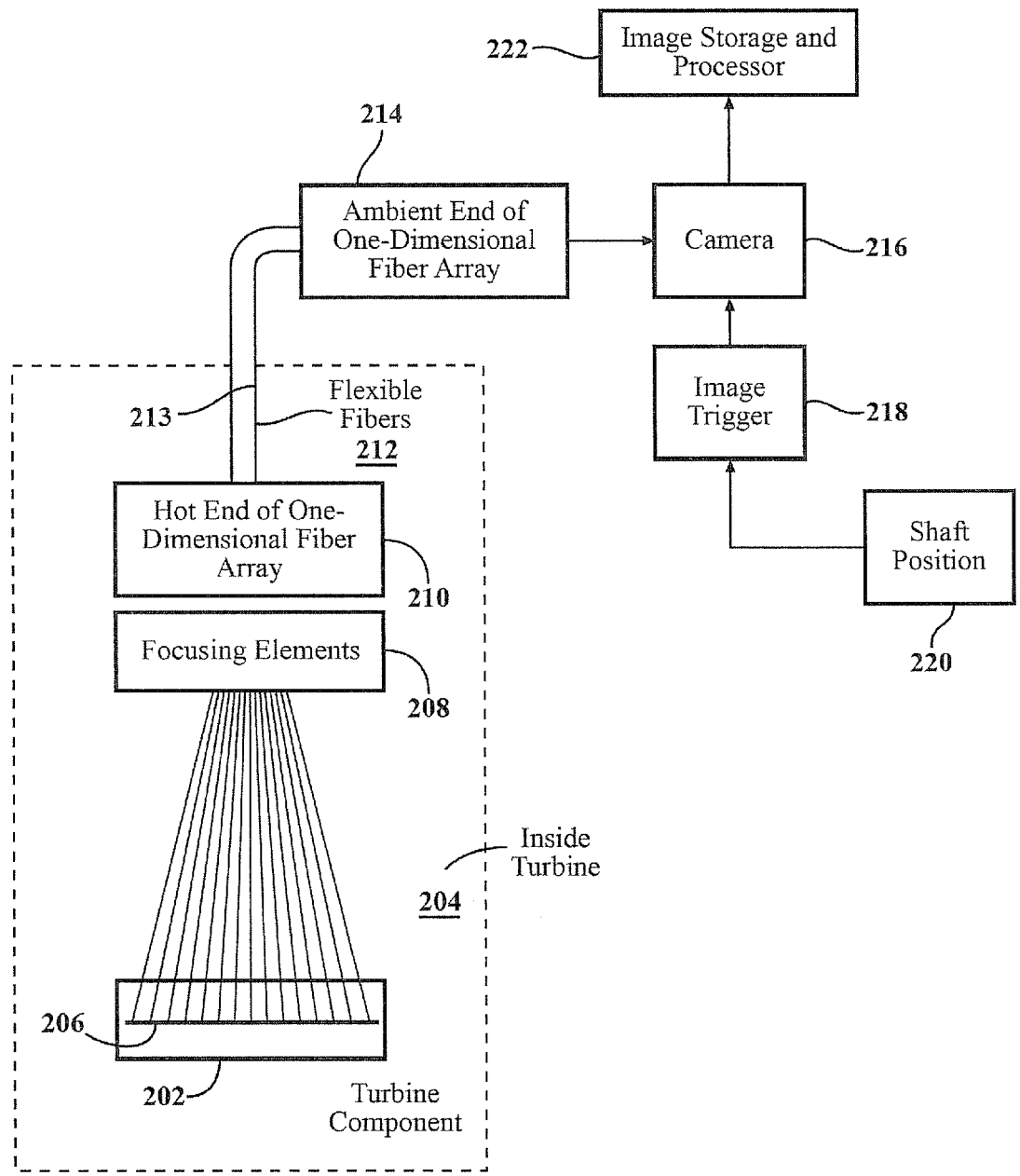
FIG. 2 is a functional block diagram of a turbine imaging system in accordance with the principles of the present invention.

FIG. 2 is a functional block diagram of a turbine imaging system in accordance with the principles of the present invention. In FIG. 2, there is an internal component 202 of the turbine which is to inspected or captured in an image. For this purpose, focusing elements 208 and a fiber array 210 and flexible optical fibers 212 are sized and positioned such that they fit inside a region 204 which is inside the turbine. In particular, the flexible optical fibers 212 are arranged side-by-side in a one-dimensional array or line 210. The other ends of the flexible optical fibers 212 also extend outside the turbine to another one-dimensional array 214. Herein, the one-dimensional array 210 within the turbine is referred to as the "hot" end of the fibers 212 and the one-dimensional array 214 outside the turbine is referred to as the "ambient" end of the fibers 212. The optical fibers 212 may, for example, be about 10 m in length and may be routed through existing channels and regions within the turbine so as not to interfere with the operation of the turbine. In some circumstances, a new channel and pathway for the optical fibers 212 may be created within the stationary components of the turbine if existing pathways do not permit a desired component of the turbine to be imaged.

One of ordinary skill will recognize that various combinations of focusing elements 208 can be selected so that an image area 206 can be defined on the turbine component 202. Depending on the desired size and location of the image area 206, as well as the distance from the fiber array 210 from the component 202, the lenses and other focusing elements 208 can be selected to achieve a desired result.

By arranging the flexible fibers 212 into a one-dimensional array 210 at the hot end, the image area 206 can resemble a line. To accomplish this configuration, the ends of the fibers are aligned next to one another and held in place by a semi-rigid housing or body constructed from materials that can withstand about 700° C. In accordance with an exemplary embodiment, depending on various factors, including the position of the array 210, i.e., a distance from the array 210 to an object plane defined on a surface being monitored, and the magnification of the focusing elements, the width of the line 206 at an object plane defined on a surface being monitored may be about 0.05 mm. Similarly, the length of the line 206 depends on various factors including the distance from the array 210 to the object plane, the magnification of the focusing elements, as well as the number of fibers selected for the one-dimensional array 210. While more fibers provide a greater image area 206 and potentially more resolution, adding more fibers makes the size of the array 210 larger such that it is more difficult to position it within some areas inside the turbine. Thus, selecting between about 30 to about 40 fibers provides a beneficial balance between size and function. One technique to increase the temperature that the flexible optical fibers can withstand is to coat the fibers with one or more group 11 transition metal. Group 11 transition metals include the traditional coinage metals such as gold, silver and copper. Other metals providing similar protective properties may be used as well. An exterior coating of metal that increases a fiber's outside diameter from about 145 μm to about 155 μm provides beneficial temperature protection. Temperature protection above 550° C., and even 700° C., can be achieved in this manner. This coating can extend from the array 210 to a part 213 of the flexible fibers 212 that is further from the hotter regions of the turbine.

At the ambient end of the fibers 212, there is also the one-dimensional array 214 that provides an output signal corresponding to the image area 206. For example, the ambient end of the fibers 212 at the one-dimensional array 214 preferably may have a one-to-one correspondence, in number and relative position, to the hot end of the fibers 212 at the one-dimensional array 210. If passive lighting (i.e., no external lighting) is used, then the infrared energy at the image area 206 is focused onto the hot ends of the fibers at the one-dimensional array 210 and then conveyed to the ambient ends of the optical fibers 212 at the other one-dimensional array 214. If active lighting is used such that an external light (not shown) is used to illuminate the image area 206, then both the radiated energy and the reflected energy will be captured by the fibers and conveyed to their respective ambient ends. For active lighting, a light source (not shown) at the ambient end would be in communication with a separate optical fiber that follows the path of the other optical fibers 212 in order to convey illuminating energy to the image area 206.

A camera 216 is coupled with the ambient end one-dimensional array 214 so that the signals representing the image area 206 can be captured at a particular instant in time. A camera 216 having a fast integration time, such as for example 3 μs, is beneficial for capturing images quickly. The one-dimensional image captured by the camera 216 can then be stored in computer accessible memory and made available to processes which can manipulate and analyze the images. These images are also made available for inspection by personnel such as designers and technicians that are interested in the operating characteristics of the turbine.

Some of the more difficult components within the hot side of a turbine to inspect include the rotating disks and attachments to these disks. Thus, embodiments contemplate an image triggering mechanism 218 that accurately and precisely controls the camera 216 to acquire an image at a desired instant in time. One signal already generated by typical turbines is a shaft position signal 220 that indicates the shaft is in a "home" position, or some other known position. Based on the shaft position signal, the speed of rotation of the shaft can be determined and thus an image trigger signal can be generated such that the position of the image area 206 is controlled to capture an image at a specific, desired shaft rotational position.

In particular, the one-dimensional fiber array 210 can be positioned so that the image area 206 is located on the circumferential surface of a rotating component of the turbine. As the component rotates, a different portion of its circumferential surface aligns within the image area 206 at different times. By capturing a succession of one-dimensional image areas 206, the entire circumferential surface of the rotating component can be imaged by the stationary one-dimensional fiber array 210. The image storage and processor 222 can store these series of images and stitch together the one-dimensional images into a two-dimensional image that is a two-dimensional panorama of the circumferential surface of the rotating component.

Figure 3:
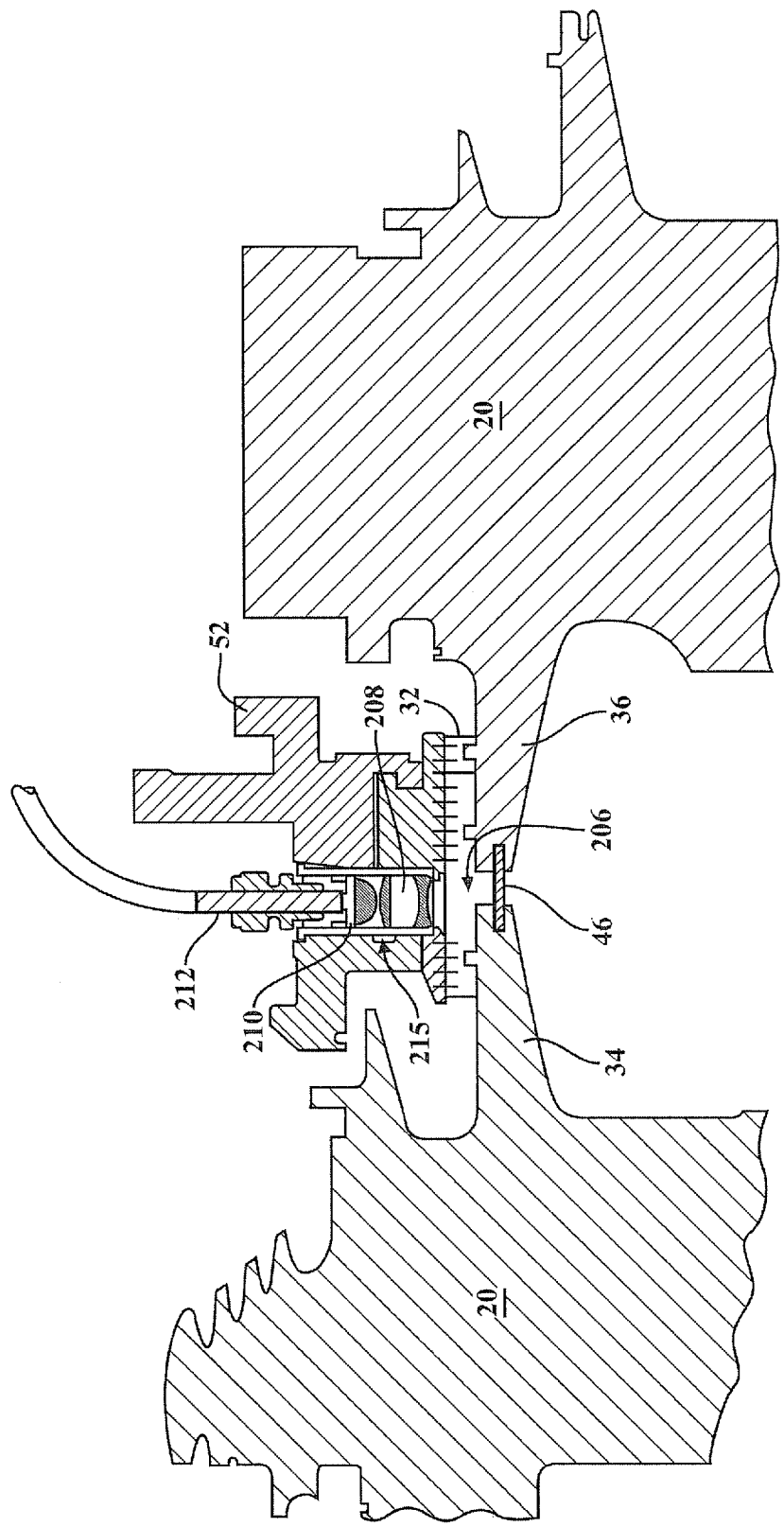
FIG. 3 is a sectional view of an area of a turbine near the intersection of two disks in which an image acquisition device is positioned in accordance with the principles of the present invention.

FIG. 3 is a sectional view of an area of a turbine near the intersection of two disks in which an image acquisition device is positioned in accordance with the principles of the present invention. The one dimension fiber array 210 and the focusing elements 208 define an imaging assembly 215, and are seen from the front of the array 210, i.e., viewing the length dimension of the array 210, and are positioned so that the image area 206 overlays where the two disk arms 34, 36 are adjacent to one another including the belly band 46. The array 210 and fibers 212 can be routed, for example, radially inwardly through a portion of a vane 16 (also see FIG. 1) into the interstage seal disk housing 52 or its supporting structure. For example, many turbine vanes consist of one or more hollow vane inserts or channels that provide passages for cooling gases. The fibers 212 and array 210 can be sized so as to fit within or through a vane cooling passage. Various insertion channels and routes can be selected and constructed without departing from the scope of the present invention. The one-dimensional fiber array 210 may be configured with a generally rectangular cross-section. Further, by sizing the one dimensional fiber array 210 to have a maximum outside dimension of about 8 mm, e.g., having a length dimension of less than 8 mm, and by providing flexible optical fibers, many different paths are available to position the array 210 as shown in FIG. 3, possibly including already existing inspection ports and channels.

As for a height above the image area 206, about 5 cm allows small enough optics to be used to produce an image area 206 of about 0.05 mm in width and about 20 to 40 mm in length. The circumference of a turbine's belly band region can be several meters; thus, more than a thousand one-dimensional images can be captured and stitched together in order to characterize the two-dimensional circumferential surface of this region.

Many turbines have hydraulic controls that automatically shift the position of the turbine rotor based on the operating conditions. In particular, when the turbine is at its fully heated operating temperature, the rotor can be shifted towards the compressor end so that the radial gaps above the turbine blade tips are reduced. The size of the image area 206 can be selected so that the interface between the two adjacent disk arms 34 and 36 remains within the image area 206 regardless of the turbine's rotor position.

Figure 4:
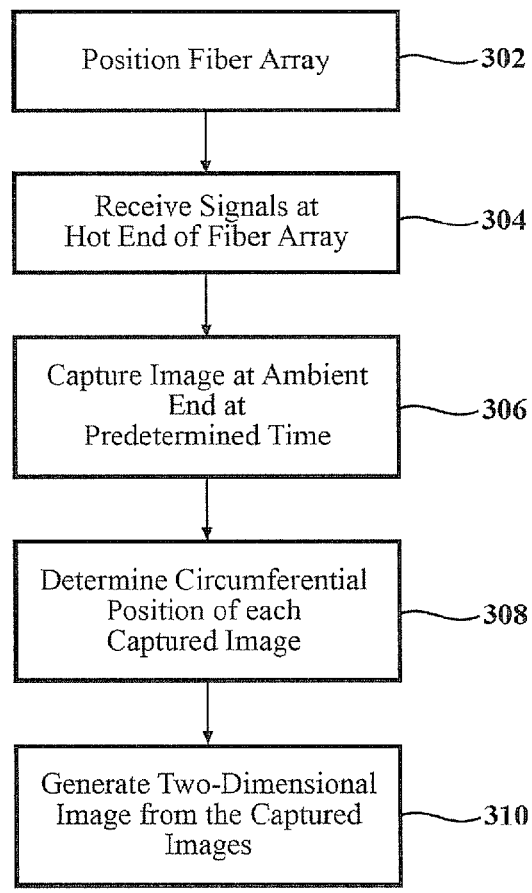
FIG. 4 is a flowchart of an exemplary process for visually inspecting regions of a turbine in accordance with the principles of the present invention.

FIG. 4 is a flowchart of an exemplary process for visually inspecting regions of a turbine in accordance with the principles of the present invention. As an initial step, a one-dimensional fiber array is positioned within a turbine such that a portion within a high temperature region (e.g., above 550° C.) can be observed during operation of the turbine. In particular, the one-dimensional fiber is positioned so that it receives radiated or reflected energy from an image area of a component of the turbine. Infrared energy in the range of about 1.6 to 1.65 μm is compatible with many types of optical fibers. Thus, during operation of the turbine, the component emits infrared and other energy that is received, in step 304, at the ends of the one-dimensional fiber array referred to as the hot end. By the nature of flexible optical fibers, the respective energy at each fiber is conveyed to the respective ends of each fiber at the ambient end of the one-dimensional array.

In step 306, an image of the ambient end of the one-dimensional fiber array is captured by a camera. This image corresponds to the image area on the component within the turbine. In this way, a visual inspection and image of the component within the high temperature region of a turbine can be acquired during operation of the turbine. In the case of a rotating component, the image can be captured at a controlled time so that the image corresponds to a known shaft rotational position. Thus, in step 308, the circumferential position of a captured image can be determined. In this way, a circumferential map or panorama of the rotating component can be constructed, in step 310, by combining the one-dimensional images together such that they are ordered in their circumferential position.

Figure 5:
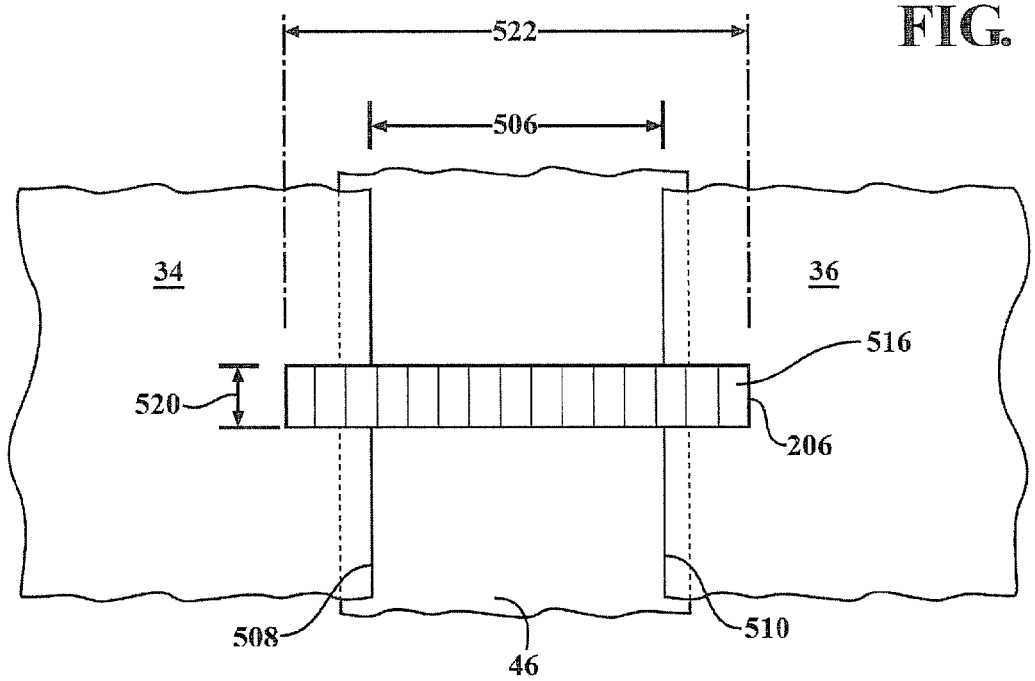
FIG. 5 is a top view, in a radial inward direction, of an area of a turbine being imaged in accordance with the principles of the present invention.

FIG. 5 is a top view, as viewed radially inwardly, of an area of a turbine being imaged in accordance with the principles of the present invention, such as to make a spatial measurement as exemplified by a gap distance 506. As shown, an interface region of two adjacent disk arms 34, 36 includes a view of a portion of the belly band 46 as well. The image area 206 includes a number of individual pixels 516 that each respectively correspond to an optical fiber in the one-dimensional fiber array 210. Furthermore, the image area 206 overlays a left disk edge 508 and a right disk edge 510. The image area 206 also overlays a portion of the belly band 46.

When a series of one-dimensional images are captured with the configuration of FIG. 5 of a rotating turbine, a number of different component attributes can be inspected. The gap distance 506 between two adjacent disk arms 34, 36 can be determined at multiple points around the circumference of their interface by capturing a series of one-dimensional images at controlled time instances. When a two-dimensional image is constructed from this series of images, the detected gap distance 506 can be compared to an allowed maximum value and minimum value to determine if the gap distance 506 is within tolerance. Additionally, the consistency of the gap distance 506 can be determined around the circumference of the interface between the two disk arms 34, 36. In addition to the gap distance 506, the condition of the belly band 46 can be observed around its circumference. Wear and deterioration of the band 46 or its attaching mechanisms can be observed, or interpreted from the captured images, without stopping operation of the turbine.

In order to increase the contrast between the disk arms 34, 36 and the belly band 46, one or more of the surfaces can be modified to increase their emissivity in the energy range conveyed by the optical fibers and captured by the camera. For instance the disk edges 508, 510 can be painted with a paint that increases infrared emissivity such that these structures would contrast with the belly band 46 in a captured image. Additionally, one or more "markers" could be placed around the disk edges 508, 510 using paint. When these markers are detected in the captured images, then they indicate that the desired image area is in focus and is being captured. If none, or only one marker is being captured in the images, then the desired image area is out of the focus of the one-dimensional fiber array.

Also, as a frame of reference, the image area 206 has a width dimension 520 and a length dimension 522. The frame of reference provided by the width dimension 520 and the length dimension 522 may be used, for example, in stitching the captured images and determining gap distances 506.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inspecting a turbine, comprising:
    positioning respective first ends of a plurality of optical fibers within a high temperature region of the turbine, the respective first ends aligned next to one another as a first one-dimensional array;
    receiving, at the respective first ends, energy emitted from an image area on a component of the turbine, the image area comprising substantially a line;
    conveying the energy received at the respective first ends to respective second ends of the plurality of optical fibers, the respective second ends aligned as a second one-dimensional array and located outside of the high temperature region of the turbine; and
    capturing, with a camera, an image simultaneously of each of the respective second ends.

2. The method of claim 1, wherein the line is about 0.05 mm in width.

3. The method of claim 1, wherein the line is between about 20 mm and about 40 mm in length.

4. The method of claim 1, wherein the component of the turbine includes at least a portion of an interface area between two adjacent disks, and the capturing an image of the respective second ends comprises determining a gap dimension defined at the interface area.

5. The method of claim 1, wherein the component of the turbine includes at least a portion of a belly band.

6. The method of claim 1, wherein the high temperature region of the turbine has a temperature above about 450° C. when the turbine is operating.

7. The method of claim 1, wherein the component is a rotating component inside an operating turbine that rotates as a result of a rotating shaft of the turbine.

8. The method of claim 7, wherein capturing an image of the respective second ends further includes:
    capturing a plurality of images of the respective second ends;
    determining a corresponding rotational position of the rotating shaft for each of the plurality of images; and
    creating, with an image processor, a two-dimensional image of the rotating component by arranging the plurality of images in order according to the respective corresponding rotational position for each of the plurality of images.

9. The method of claim 1, further comprising:
    coating an exterior portion of the plurality of fibers with one or more group 11 transition metals.

10. The method of claim 1, wherein a maximum outside dimension of the first one-dimensional array is about 8 mm.

11. A system for inspecting a turbine, comprising:
    a plurality of optical fibers having respective first ends positioned within a high temperature region of the turbine and having respective second ends positioned outside of the high temperature region of the turbine;
    wherein the respective first ends are aligned next to one another in a first one-dimensional array;
    wherein the respective second ends are aligned in a second one-dimensional array;
    the first one-dimensional array configured to receive, at the respective first ends, energy emitted from an image area on a component of the turbine, the image area comprising substantially a line, wherein the plurality of optical fibers are configured to convey the energy received at the respective first ends to the respective second ends; and
    a camera configured to simultaneously capture an image of each of the respective second ends.

12. The system of claim 11, wherein the line is about 0.05 mm in width.

13. The system of claim 11, wherein the line is between about 20 mm and about 40 mm in length.

14. The system of claim 11, wherein the component of the turbine includes at least a portion of an interface area between two adjacent disks.

15. The system of claim 11, wherein the component of the turbine includes at least a portion of a belly band.

16. The system of claim 11, wherein the high temperature region of the turbine has a temperature above about 450° C. when the turbine is operating.

17. The system of claim 11, wherein the component is a rotating component inside an operating turbine that rotates as a result of a rotating shaft of the turbine.

18. The system of claim 17, further comprising:
a shaft position signal generator configured to generate a position signal indicating a predetermined rotational position of the rotating shaft;
a trigger signal generator configured to transmit a trigger signal to the camera to capture the image of the second ends, wherein the trigger signal generator transmits a plurality of trigger signals to cause the camera to capture a plurality of images of the respective second ends;
the trigger signal generator further configured to transmit each of the plurality of trigger signals at a respective time based on the position signal so that each respective trigger signal corresponds to a respective rotational position of the shaft; and
an image analyzer configured to create a two-dimensional image of the rotating component by arranging the plurality of images in order according to the respective corresponding rotational position for each of the plurality of images.

19. A method of inspecting an operating turbine, comprising:
positioning respective first ends of a plurality of optical fibers within a high temperature region of the turbine;
receiving, at the respective first ends, energy emitted from an image area on a component of the turbine;
routing the plurality of optical fibers through a vane of the turbine;
conveying the energy received at the respective first ends to respective second ends of the plurality of optical fibers, the respective second ends located outside of the high temperature region of the turbine; and
capturing, with a camera, an image simultaneously of each of the respective second ends.

20. The method of claim 19, wherein the respective first ends are aligned in a one-dimensional array.

\* \* \* \* \*